(12) United States Patent
Miyoshi et al.

(10) Patent No.: US 8,609,886 B2
(45) Date of Patent: Dec. 17, 2013

(54) METHOD FOR PRODUCING HIGH PURITY TERMINAL OLEFIN COMPOUND

(75) Inventors: Kei Miyoshi, Niigata (JP); Goro Asanuma, Niigata (JP)

(73) Assignee: Kuraray Co., Ltd. (JP)

( * ) Notice: Subject to any disclaimer, the term of this patent is extended or adjusted under 35 U.S.C. 154(b) by 188 days.

(21) Appl. No.: 13/262,372

(22) PCT Filed: Jan. 8, 2010

(86) PCT No.: PCT/JP2010/050169
§ 371 (c)(1),
(2), (4) Date: Sep. 30, 2011

(87) PCT Pub. No.: WO2010/113531
PCT Pub. Date: Oct. 7, 2010

(65) Prior Publication Data
US 2012/0029229 A1 Feb. 2, 2012

(30) Foreign Application Priority Data
Mar. 31, 2009 (JP) .................. 2009-085898

(51) Int. Cl.
*C07C 67/48* (2006.01)

(52) U.S. Cl.
USPC .................................................. 560/218

(58) Field of Classification Search
USPC .................................................. 560/218
See application file for complete search history.

(56) References Cited

U.S. PATENT DOCUMENTS

| | | | |
|---|---|---|---|
| 3,306,946 A | 2/1967 | Snyder et al. | |
| 4,471,152 A | 9/1984 | Doyle et al. | |
| 4,510,331 A | 4/1985 | Yoshimura et al. | |
| 4,710,273 A | 12/1987 | Okamoto | |
| 5,057,644 A | 10/1991 | Lin et al. | |
| 5,994,590 A * | 11/1999 | Tsuda et al. | 568/450 |
| 6,175,050 B1 | 1/2001 | Slaugh et al. | |

FOREIGN PATENT DOCUMENTS

| | | |
|---|---|---|
| EP | 69339 A2 | 1/1983 |
| JP | 62-060378 A | 3/1987 |
| JP | 02-218638 A | 8/1990 |
| JP | 06-210173 A | 8/1994 |
| JP | 2002544182 U | 12/2002 |
| WO | 9209546 A1 | 6/1992 |

OTHER PUBLICATIONS

Mihailovic, et al., "The conversion of primary alcohols to the corresponding aldehydes by a modified leadtetraacetate oxidation," Tetrahedron Letters, Pergamon Journals, Ltd. (1986): vol. 27, No. 20; pp. 2287-2290.

Bestmann, et al., "Pheromone XX 1), synthese von (e)-8,(e)-10-dodecadien-1-ol (codlemone), dem sexuallockstoff des apfelwicklers, seiner isomeren, homologen and derivate," Tetrahedron Letters, Pergamon Journals, Ltd. (1986): No. 36; pp. 3329-3332.

* cited by examiner

*Primary Examiner* — Yong Chu
*Assistant Examiner* — Karen Cheng
(74) *Attorney, Agent, or Firm* — Fox Rothschild LLP; Peter J. Butch, III; Robert N. Henrie, II

(57) ABSTRACT

An industrially advantageous method for producing a high purity terminal olefin is disclosed, comprising the steps of (a) contacting a mixture comprising a terminal olefin represented by formula (1):

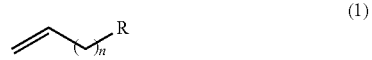

(1)

and one or more corresponding internal olefins as impurities, with a brominating agent in the presence of water or an alcohol, to convert the internal olefin(s) to compound(s) having a higher boiling point than the terminal olefin; and (b) purifying the terminal olefin by distillation from the reaction mixture.

7 Claims, No Drawings

METHOD FOR PRODUCING HIGH PURITY TERMINAL OLEFIN COMPOUND

CROSS REFERENCE TO RELATED APPLICATION

The present application is a 35 U.S.C. §371 National Phase application of International Application Serial No. PCT/JP10/50169, filed Jan. 8, 2010, which claims priority to Japanese Application Serial No. 2009-085898, filed Mar. 31, 2009. The disclosures of both applications are incorporated herein by reference in their entirety.

TECHNICAL FIELD

The present invention relates to a method for producing a high purity terminal olefin compound. Specifically, the present invention relates to a method for producing a high purity terminal olefin compound by distilling a mixture containing a terminal olefin compound and a corresponding internal olefin compound as an impurity. The high purity terminal olefin compound to be obtained by the present invention is useful as an intermediate in organic synthesis (for example, a synthetic intermediate, in particular, for medicinal products where contamination of impurities is hardly accepted).

BACKGROUND ART

The terminal olefin compound is a generic term for a compound in which a double bond is present between two carbon atoms locating in the terminal of a hydrocarbon chain, and various terminal olefin compounds have been used for the intended purpose such as intermediates for organic syntheses.

As one of the terminal olefin compounds, there is, for example, 7-octenal represented by the following chemical formula 2.

[Chemical Formula 2]

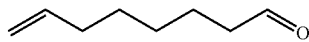

Previously, as a production method for 7-octenal, the following methods have been known, that is, 1) a synthetic method from 2,7-octadien-1-ol with a metal catalyst (see Patent Literatures 1 to 4); 2) a synthetic method by oxidizing 7-octenol (see Non-Patent Literature 1); 3) a synthetic method by hydroborating 1,7-octadiene, and subsequently oxidizing using pyridinium chlorochromate (see Non-Patent Literature 2); and the like.

PRIOR ART LITERATURES

Patent Literature

Patent Literature 1: JP-B-62-060378;
Patent Literature 2: JP-A-2-218638;
Patent Literature 3: JP-A-6-210173;
Patent Literature 4: EP No. 69339.

Non-Patent Literature

Non-Patent Literature 1: Tetrahedron Letters, 1986, Vol. 20, p. 2287;
Non-Patent Literature 2: Tetrahedron Letters, 1978, Vol. 36, p. 3329.

SUMMARY OF INVENTION

Problem to be Solved by the Invention

However, from the study by the present inventors, it has been clarified that any of the heretofore known techniques is still insufficient in the viewpoint of obtaining a high purity 7-octenal. Specifically, firstly in the above-described method 1), it has been found that by-products such as cis- and/or trans-6-octenal (hereinafter, these compounds are also collectively referred to simply as "6-octenal") represented by the following chemical formula 3 are formed together with 7-octenal, to lower purity of 7-octenal (content ratio of 6-octenal to 7-octenal is around 0.5 to 10% by mass as a total amount of cis- and trans-isomers).

[Chemical Formula 3]

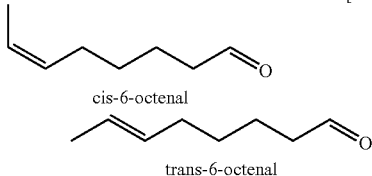

In particular, among the impurities, 6-octenal has little difference in boiling point from 7-octenal. In more detail, the relative volatility of cis-6-octenal to 7-octenal is 1.06, and the relative volatility of trans-6-octenal to 7-octenal is 1.13. Therefore, it is difficult to separate 6-octenal and 7-octenal by usual method such as distillation, and thus it has been found that it is difficult to obtain a high purity 7-octenal.

In addition, in the above-described method 2), 7-octenol is used as a raw material, but commercially available 7-octenol contains 6-octenol. For this reason, 7-octenal to be obtained by the method 2) inevitably contains as a by-product 6-octenal (see the above-described chemical formula 3) which is formed by oxidation of 6-octenol. As described above, it is difficult to separate this 6-octenal as a by-product from 7-octenal by the common method, and hence it is also difficult to obtain a high purity 7-octenal by the method 2).

Further, in the above-described method 3), a lot of industrially unfavorable processes have been employed, where for example, a reagent to be used is expensive and has high environmental load, as exemplified in hydroboration and oxidation using pyridinium chlorochromate.

In such way, until now, it is present situation that an industrially advantageous means to obtain a high purity purified 7-octenal has not been established. And such a problem in the separation and purification of 7-octenal from 6-octenal possibly occurs similarly when another terminal olefin compound is separated and purified from a corresponding internal olefin compound.

Therefore, the present invention is directed to provide an industrially advantageous means to obtain a high purity terminal olefin compound (for example, 7-octenal).

Means for Solving the Problem

The present inventors have intensively studied to solve the above-described problem, as a result, have found that, when a terminal olefin compound is purified from a mixture containing a terminal olefin compound (for example, 7-octenal) and a corresponding internal olefin compound (for example, 6-octenal) as an impurity, the terminal olefin compound can be efficiently separated from the internal olefin compound as an impurity, by bringing the relevant mixture into contact with a brominating agent in the presence of water or an alcohol to convert the internal olefin compound to a compound having a higher boiling point, and subsequently carrying out distillation, and completed the present invention.

That is, the method for producing a high purity terminal olefin compound of the present invention comprises a step where a mixture containing a terminal olefin compound represented by the following chemical formula 1:

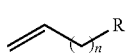

[Chemical Formula 1]

[Wherein n represents an integer of 1 to 6, R represents —CH$_2$CH$_3$, —CH=CH$_2$, —CH$_2$CN, or a group represented by the general formula —CH$_2$COR$^1$ (wherein R$^1$ represents hydrogen atom, alkyl group having 1 to 8 carbon atoms, cycloalkyl group having 3 to 8 carbon atoms, or alkoxy group having 1 to 8 carbon atoms)]; and a corresponding internal olefin compound as an impurity is brought into contact with a brominating agent in the presence of water or an alcohol, to convert the internal olefin compound to a compound having a higher boiling point; and a step where the terminal olefin compound is purified by distillation from the obtained mixture.

Effect of the Invention

According to the present invention, an industrially advantageous means to obtain a high purity terminal olefin compound can be provided.

EMBODIMENTS FOR CARRYING OUT THE INVENTION

Hereinafter, the method for producing a high purity terminal olefin compound of the present invention will be explained in detail.

In the method for producing a high purity terminal olefin compound of the present invention, a terminal olefin compound is purified by distilling a mixture containing the terminal olefin compound and an internal olefin compound as an impurity. With this procedure, a high purity terminal olefin compound is produced.

That is, in the present invention, an object substance to be purified is a terminal olefin compound containing an internal olefin compound as an impurity. In the production method of the present invention, a terminal olefin compound, which is an object substance to be purified, is represented by the following chemical formula 1.

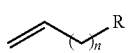

[Chemical Formula 1]

In the chemical formula 1, n represents an integer of 1 to 6, preferably 3 to 6, more preferably 4 to 6, and particularly preferably 5.

In addition, in the chemical formula 1, R represents —CH$_2$CH$_3$, —CH=CH$_2$, —CH$_2$CN, or a group represented by the general formula —CH$_2$COR$^1$. Among them, R is preferably a group represented by the general formula —CH$_2$COR$^1$.

In the general formula —CH$_2$COR$^1$, R$^1$ represents hydrogen atom, alkyl group having 1 to 8 carbon atoms, cycloalkyl group having 3 to 8 carbon atoms, or alkoxy group having 1 to 8 carbon atoms. Among them, R$^1$ is preferably hydrogen atom or alkyl group having 1 to 8 carbon atoms, and particularly preferably hydrogen atom.

The alkyl group having 1 to 8 carbon atoms represented by R$^1$ includes, for example, methyl group, ethyl group, n-propyl group, isopropyl group, n-butyl group, isobutyl group, sec-butyl group, tert-butyl group, n-pentyl group, isopentyl group, neopentyl group, 3-pentyl group, n-hexyl group, 3-methyl-1-pentyl group, n-heptyl group, 4-heptyl group and n-octyl group. In addition, the cycloalkyl group having 3 to 8 carbon atoms represented by R$^1$ includes, for example, cyclopropyl group, cyclobutyl group, cyclopentyl group, cyclohexyl group, and the like. Further, the alkoxy group having 1 to 8 carbon atoms represented by R$^1$ includes alkoxy group corresponding to the above-described alkyl group having 1 to 8 carbon atoms.

Specific example of the compound represented by the chemical formula 1 includes, for example, aldehyde compound such as 7-octenal, 8-nonenal, 6-heptenal, 5-hexenal and 4-pentenal; nitrile compound such as 7-octenonitrile, 8-nonenonitrile, 6-heptenonitrile, 5-hexenonitrile and 4-pentenonitrile; alkenes such as 1,7-octadiene, 1,8-nonadiene, 1,6-heptadiene, 1,5-hexadiene, 1,4-pentadiene, 1-octene, 1-nonene, 1-heptene, 1-hexene and 1-pentene; ketones such as 7-heptenyl methyl ketone, 7-heptenyl ethyl ketone, 7-heptenyl butyl ketone, 7-heptenyl n-propyl ketone, 7-heptenyl isopropyl ketone, 8-octenyl methyl ketone, 8-octenyl ethyl ketone, 8-octenyl butyl ketone, 8-octenyl n-propyl ketone, 8-octenyl isopropyl ketone, 6-hexenyl methyl ketone, 6-hexenyl ethyl ketone, 6-hexenyl butyl ketone, 6-hexenyl n-propyl ketone, 6-hexenyl isopropyl ketone, 5-pentenyl methyl ketone, 5-pentenyl ethyl ketone, 5-pentenyl butyl ketone, 5-pentenyl n-propyl ketone, 5-pentenyl isopropyl ketone, 4-butenyl methyl ketone, 4-butenyl ethyl ketone, 4-butenyl butyl ketone, 4-butenyl n-propyl ketone and 4-butenyl isopropyl ketone; esters such as methyl 7-octenoate, ethyl 7-octenoate, butyl 7-octenoate, n-propyl 7-octenoate, isopropyl 7-octenoate, methyl 8-nonenoate, ethyl 8-nonenoate, butyl 8-nonenoate, n-propyl 8-nonenoate, isopropyl 8-nonenoate, methyl 6-heptenoate, ethyl 6-heptenoate, butyl 6-heptenoate, n-propyl 6-heptenoate, isopropyl 6-heptenoate, methyl 5-hexenoate, ethyl 5-hexenoate, butyl 5-hexenoate, n-propyl 5-hexenoate, isopropyl 5-hexenoate, methyl 4-pentenoate, ethyl 4-pentenoate, butyl 4-pentenoate, n-propyl 4-pentenoate, isopropyl 4-pentenoate, and the like; and so on. Among them, the compound represented by the chemical formula 1 is preferably 7-octenal, 8-nonenal, 6-heptenal, 5-hexenal and 4-pentenal, more preferably 7-octenal, 8-nonenal, 6-heptenal and 5-hexenal, particularly preferably 7-octenal, 8-nonenal and 6-heptenal, and most preferably 7-octenal.

In the production method of the present invention, the above-described compound represented by the chemical formula 1 is separated from a corresponding internal olefin compound contained as an impurity. It should be noted that "a corresponding internal olefin compound" means a compound which has the same structure as the terminal olefin compound except that a double bond is present inside of the carbon atom skeleton (that is, at a position other than the terminal double bond). Therefore, any compound can be included in the concept of "internal olefin compounds", so long as it satisfies this definition. It should be noted that sometimes the internal olefin compound includes cis- and trans-isomers, but either of these isomers is included in the internal olefin compound. For example, when the production method of the present invention is practiced using 7-octenal as the terminal olefin compound, the above-described 6-octenal (that is, cis-6-octenal and trans-6-octenal) is firstly included as the internal olefin compound. However, besides this, when 5-octenal, 4-octenal and the like are contained in the mixture, these compounds can also be included in the concept of the internal olefin compound including both of cis- and trans-isomers thereof.

In this regard, however, when a terminal olefin compound is produced, as described above, an internal olefin compound, in which a double bond exists between the carbon atoms at position-2 and position-3 from the terminal in the side where the terminal double bond locates in the terminal olefin compound, tends to be formed as an impurity. Therefore, the internal olefin compound contained as an impurity in the terminal olefin compound represented by the chemical formula 1 is preferably a compound represented by the following chemical formula 4.

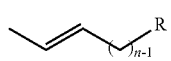

[Chemical Formula 4]

In chemical formula 4, since definitions and preferable embodiments of n and R are same as those in chemical formula 1, detailed explanation will be omitted here.

Source of the "mixture containing a terminal olefin compound and an internal olefin compound as an impurity" is not particularly limited. As a preferable example, it is particularly useful to use a reaction solution containing a terminal olefin compound obtained in various types of reactions as it is, as said mixture. As a matter of course, as this mixture, it is no problem to use a mixture in which impurities or the like other than those having a boiling point close to that of the target have been removed by distillation or the like in advance.

Just to be sure, techniques for producing a terminal olefin compound will be briefly explained, taking the case of producing 7-octenal as an example. As a technique for producing 7-octenal, it is industrially advantageous to employ, for example, the following techniques, that is, 1) synthesis from 2,7-octadien-1-ol using a metal catalyst; or 2) oxidation of 7-octenol. Among these techniques, it is preferable to use the technique of 1) from the viewpoints that step is short and that synthesis in an industrial scale is possible. It should be noted that technical scope of the present invention is not influenced at all by the technique per se for producing the terminal olefin compound (for example, 7-octenal). Therefore, a reaction solution containing a terminal olefin compound produced by another technique than these may be used, or a reaction solution containing a terminal olefin compound to be produced by a technique which will be newly developed in future may be used. As described above, production technique for a terminal olefin compound which is a target of purification was explained taking the case of producing 7-octenal as an example. However, as for production technique for other terminal olefin compounds, the heretofore known knowledge can also be referred to. As one example, a terminal olefin compound having a nitrile group at the terminal (for example, 7-octenonitrile) can be produced by reacting a corresponding terminal olefin aldehyde (for example, 7-octenal) with hydroxylamine salts such as hydroxylamine sulfate, and then dehydrating. In addition, as an additional explanation taking 1,7-octadiene as a terminal olefin compound having a double bond at the other terminal too as an example, 1,7-octadiene can be produced by reacting 2,7-octadien-1-ol with formic acid to be formylated, and then heating this compound in the presence of a metal catalyst such as a palladium catalyst. Further, a terminal olefin compound (for example, methyl 7-octenoate) having an alkyl ester group at the terminal can be produced by oxidizing a corresponding terminal olefin aldehyde (for example, 7-octenal) to be converted to a carboxylic acid, and subsequently reacting the carboxylic acid with an alcohol (for example, methanol when methyl ester is obtained) corresponding to the alkyl site of the alkyl ester to be esterified.

As described above, embodiments where a reaction solution in production of a terminal olefin compound is used as it is as the "mixture" in the production method of the present invention were explained, but the mixture is not limited only to such embodiments. In some cases, for example, the present invention can be applied to an embodiment where a mixture containing a terminal olefin compound and an internal olefin compound as an impurity is added to an appropriate solvent separately, and then the distillation procedure described later is carried out.

In the mixture containing a terminal olefin compound and an internal olefin compound as an impurity, content of said internal olefin compound is not particularly limited. Usually, the terminal olefin compound is contained in around 90 to 98% by mass, and the internal olefin compound is contained in around 1 to 10% by mass, relative to 100% by mass of the mixture.

In the production method for a terminal olefin compound of the present invention, the mixture arranged or prepared as described above is brought into contact with a brominating agent in the presence of water or an alcohol. By this procedure, the internal olefin compound contained in the relevant mixture is converted to a compound having a higher boiling point.

The brominating agent to be used in the present step is not particularly limited. Those generally used in the technical field of synthetic organic chemistry for bromoalkoxylation or bromohydroxylation of a C—C double bond can be appropriately used. The brominating agent usable in the present step includes, for example, N-bromoimide compound such as N-bromosuccinimide and N-bromophthalimide; dibromohydantoin compound such as 1,3-dibromohydantoin and 5,5-dimethyl-1,3-dibromohydantoin; hypobromite such as sodium hypobromite and potassium hypobromite; a mixture of alkali metal bromide such as potassium bromide, sodium bromide and lithium bromide and hypochlorite such as sodium hypochlorite, potassium hypochlorite and lithium hypochlorite; and the like. Among them, dibromohydantoin compound is preferably used, and 5,5-dimethyl-1,3-dibromohydantoin is particularly preferably used, from the viewpoints that it is available industrially and inexpensively as well as advantageous in volume efficiency.

The amount of the brominating agent to be used is not particularly limited, but preferably 1 to 50 moles [in bromine molecule ($Br_2$) equivalent] to 1 mole of the internal olefin compound contained in the mixture.

In the present step, the treatment with the brominating agent is carried out in the presence of water or an alcohol. With this procedure, the internal olefin compound contained in the mixture is bromoalkoxylated (in the presence of alcohol) or bromohydroxylated (in the presence of water), and becomes a compound having a higher boiling point. For this reason, it is surmised that the terminal olefin compound can be purified in high purity by subsequent distillation.

In the present step, contact between the mixture and the brominating agent is carried out in the presence of water or an alcohol. In this case, the alcohol to be used is not particularly limited, and includes, for example, methanol, ethanol, n-propanol, isopropanol, n-butanol, isobutanol, sec-butanol, tert-butanol, and the like. Water or these alcohols may be used alone or in combination of two or more kinds. Among them, water, methanol or ethanol is preferably used. Amount of water or alcohol to be used is preferably equal to or more than an amount of the brominating agent to be used in molar ratio, more preferably 1 to 300 moles, further more preferably 25 to 200 moles, and particularly preferably 50 to 100 moles relative to 1 mole of the brominating agent.

Temperature for contacting the mixture with the brominating agent is also not particularly limited. However, from the viewpoint that the reaction is sufficiently progressed while formation of by-product such as acetal compound is inhibited without requiring any special facilities, the temperature for contacting the mixture with the brominating agent is preferably −78 to 20° C., and more preferably −20 to 5° C. Further, time for contacting the mixture with the brominating agent is also not particularly limited, but no later than 10 hours is sufficient, and preferably it is 1 to 5 hours.

The production method of the present invention comprises a step where the terminal olefin compound is purified by contacting the above-described mixture with the brominating agent, and then distilling the relevant mixture (that is, carrying out distillation purification).

Specific conditions of the distillation purification are not particularly limited, and a condition under which the desired terminal olefin compound can be recovered efficiently in the distillate can be appropriately set. Particularly preferable embodiment includes an embodiment where compounds having low boiling point such as solvent are firstly distilled off, and then the terminal olefin compound as a target of purification is distilled.

As one example of distillation purification conditions used when the terminal olefin compound is distilled, distillation temperature is preferably 20 to 200° C., and more preferably 50 to 150° C. In addition, pressure of the system in the distillation purification is preferably 500 to 100000 Pa. It should be noted that distillation time can vary depending on scale of the system, but is generally around 0.5 to 36 hours.

According to the production method of the present invention, a high purity terminal olefin compound is obtained by an industrially extremely advantageous technique. It should be noted that the purity of the obtained high purity terminal olefin compound is not particularly limited, but preferably 98% by mass or more, and particularly preferably 99% by mass or more. From other viewpoints, the content of the internal olefin compound is preferably 1 mol % or less, and more preferably 0.5 mol % or less relative to 1 mol of the high purity terminal olefin compound. As mentioned above, the high purity terminal olefin compound is useful as an intermediate in organic synthesis (for example, as a synthetic intermediate, in particular, for medicinal products where contamination of impurities is hardly accepted).

EXAMPLES

Hereinafter, the present invention is specifically explained by means of Examples, but the present invention is by no means limited to these Examples.

Synthesis Example 1

Synthesis of 7-octenal from 2,7-octadien-1-ol using a metal catalyst

Into a 50 mL volume four-necked flask provided with distilling apparatus, a dropping funnel, a stirrer, a thermometer and nitrogen gas introducing port, Cu/Cr oxide catalyst (N 203, produced by Nikki Chemical Co., Ltd.) [0.2 g (corresponds to 1.1% by mass relative to the reaction mixture)] and 2,7-octadien-1-ol (20.0 g) were charged. After inside of the system was sufficiently replaced with nitrogen gas, the mixture was heated up until internal temperature reached 180° C. 2,7-Octadien-1-ol (20.0 g, 0.159 mol) was added dropwise thereto over 60 minutes under stirring while nitrogen gas was introduced at a rate of 10 L/h. After completion of the addition, stirring was continued for further 60 minutes under the same conditions. Distillate (38.0 g) was obtained. The ratio of 7-octenal in the distillate to charged 2,7-octadien-1-ol was 89 mol %. Fractional distillation of this distillate was carried out. As a distillate under 66.7 kPa at 159 to 161° C., crude 7-octenal (30.5 g) (7-octenal: 90.0% in gas chromatography simple area %, cis-6-octenal: 6.3% in gas chromatography simple area %, tras-6-octenal: 4.0% in gas chromatography simple area %, and octanal: 0.1% in gas chromatography simple area %) was obtained.

Example 1

Brominating agent=5,5-dimethyl-1,3-dibromohydantoin; in the presence of methanol Into a nitrogen-substituted 500 mL volume flask, the crude 7-octenal (30.5 g) (90.0% in gas chromatography simple area %, net: 27.5 g, 0.22 mol; cis-6-octenal: 6.3% in gas chromatography simple area %, tras-6-octenal: 4.0% in gas chromatography simple area %) obtained by the technique of Synthesis Example 1, and methanol (72.7 g) were charged. After the mixture was cooled to 0° C., 5,5-dimethyl-1,3-dibromohydantoin (7.5 g, 26.2 mmol) was added thereto at a temperature in a range of 0 to 5° C. over 7 hours.

After completion of the addition, the reaction mixture was washed with 5% by mass sodium carbonate aqueous solution (95 g). Into the reaction mixture, toluene (95 g) was added, stirred for 1.0 hour, and then left as it is, to separate an organic layer. The organic layer was washed again with 5% by mass sodium carbonate aqueous solution (95 g). The organic layer was distilled under reduced pressure of 670 Pa to obtain a high purity 7-octenal (10.3 g) (purity: 99.1%, simple area ratio by gas chromatography of cis-6-octenal to 7-octenal was 0.25%, and simple area ratio by gas chromatography of trans-6-octenal to 7-octenal was 0%) as a distillate at boiling point of 47 to 49° C. It should be noted that the analysis was carried out using gas chromatography (column: CP-Sil 5CB) and tetradecane as an internal standard. The analyses described below are same.

Example 2

Brominating Agent=N-Bromosuccinimide; in the Presence of Methanol

Into a nitrogen-substituted 30 mL volume flask, the crude 7-octenal (5.4 g) (7-octenal: 90.0% in gas chromatography simple area %, net: 4.9 g, 38.8 mmol; cis-6-octenal: 6.3% in gas chromatography simple area %, tras-6-octenal: 4.0% in gas chromatography simple area %) obtained by the technique of Synthesis Example 1, and methanol (10 g) were charged. After the mixture was cooled to 10° C., N-bromosuccinimide (1.5 g, 8.4 mmol) was added thereto at a temperature in a range of 10 to 20° C. over 1.0 hour.

After completion of the addition, the crude product was quantitatively analyzed to find out 7-octenal (3.7 g) (yield:

75%; simple area ratio by gas chromatography of cis-6-octenal to 7-octenal was 0.21%, and simple area ratio by gas chromatography of trans-6-octenal to 7-octenal was 0.04%) was obtained.

Example 3

Brominating Agent=a Mixture of Potassium Bromide and Sodium Hypochlorite; in the Presence of Water Into a nitrogen-substituted 30 mL volume flask, the crude 7-octenal (5.4 g) (7-octenal: 90.0% in gas chromatography simple area %, net: 4.9 g, 38.8 mmol; cis-6-octenal: 6.3% in gas chromatography simple area %, tras-6-octenal: 4.0% in gas chromatography simple area %) obtained by the technique of Synthesis Example 1, ethyl acetate (10 g) and water (10 g) were charged. After the mixture was cooled to 10° C., KBr (1.0 g, 8.4 mmol) was added thereto. Subsequently, 2.5% by mass sodium hypochlorite aqueous solution (24 g, 8.0 mmol) was added thereto at a temperature in a range of 10 to 20° C. over 1.0 hour.

After completion of the addition, the crude product was quantitatively analyzed to find out 7-octenal (2.2 g) (yield: 45%; simple area ratio by gas chromatography of cis-6-octenal to 7-octenal was 0.35%, and simple area ratio by gas chromatography of trans-6-octenal to 7-octenal was 0.1%).

Synthesis Example 2

Synthesis of 7-octenonitrile from 7-octenal

Into a nitrogen-substituted 500 mL volume flask, toluene (200 g) and the crude 7-octenal (30.5 g) (90.0% in gas chromatography simple area %, net: 27.5 g, 0.22 mol; cis-6-octenal: 6.3% in gas chromatography simple area %, tras-6-octenal: 4.0% in gas chromatography simple area %) obtained by the technique of Synthesis Example 1 were charged. An aqueous solution of 35.5% by mass hydroxylamine sulfate (55.5 g; net: 19.7 g, 0.12 mol) was added thereto, and then the mixture was cooled to 0° C. An aqueous solution of 18% by mass sodium hydroxide (53.3 g; net: 9.6 g, 0.24 mol) was added thereto at a temperature in a range of 10 to 20° C. over 1.0 hour. After completion of the reaction, water (100 g) was added and the resulting two layers were separated. After acetic anhydride (24.5 g, 0.24 mol) was added to the organic layer, azeotropic dehydration was carried out by heating at an internal temperature of 120° C. for 3 hours. The organic layer was separated, and the obtained organic layer was distilled under a reduced pressure of 670 Pa, to obtain crude 7-octenonitrile (25.0 g) (90.2% in gas chromatography simple area %, 22.5 g, 0.18 mol; cis-6-octenonitrile: 3.9% in gas chromatography simple area %, tras-6-octenonitrile: 3.4% in gas chromatography simple area %) as a distillate.

Example 4

Brominating agent=5,5-dimethyl-1,3-dibromohydantoin; in the presence of methanol Into a nitrogen-substituted 1000 mL volume flask, the crude 7-octenonitrile (90.2% in gas chromatography simple area %, 50 g, 0.41 mol; cis-6-octenonitrile: 3.9% in gas chromatography simple area %, tras-6-octenonitrile: 3.4% in gas chromatography simple area %) obtained by the technique of Synthesis Example 2 and methanol (230 g) were charged. After the mixture was cooled to 10° C., 5,5-dimethyl-1,3-dibromohydantoin (14.3 g, 50.2 mmol) was added thereto at a temperature in a range of 10 to 20° C. over 3.0 hours.

After completion of the addition, the reaction mixture was stirred at a temperature in a range of 10 to 20° C. for 1.0 hour, and then washed with 5% by mass sodium carbonate aqueous solution (150 g). Toluene (120 g) was added thereto, stirred for 1.0 hour, and then left as it was, to separate organic layer. The organic layer was washed again with 5% by mass sodium carbonate aqueous solution (150 g). The crude product was quantitatively analyzed to find out 7-octenonitrile (35.0 g) (yield: 70%, simple area ratio by gas chromatography of cis-6-octenonitrile to 7-octenonitrile was 0.4%, and simple area ratio by gas chromatography of trans-6-octenonitrile to 7-octenonitrile was 0.1%) was obtained.

Synthesis Example 3

Synthesis of 1,7-octadiene from 2,7-octadien-1-ol through formylated 2,7-octadien-1-ol Into a 6000 L volume reactor, 2,7-octadien-1-ol (2362.6 kg, 18.72 kmol), 99% by mass formic acid (1323.1 kg, 28.56 kmol), and methyl isopropyl ketone (MIPK: 3-methyl-2-butanone) (530.4 kg) were charged, and the pressure was reduced to 53.3 kPa under stirring. After reducing the pressure, the reaction was conducted by steam heating. Progress of the reaction was monitored by gas chromatography at a predetermined time interval, and the reaction was terminated when conversion rate reached 99.5%. After completion of the reaction, formic acid and MIPK were distilled off under a reduced pressure (recovery of the raw materials). A crude product was obtained as a tank bottom (crude yield: 93.3%). The resultant crude product was transferred to 5000 L distiller and distilled, to obtain purified formylated 2,7-octadien-1-ol (yield: 72.9%).

Subsequently, into a 5000 L volume reactor, diglyme (1885 kg), a solution of 20% by mass tricyclohexylphosphine in xylene (2.84 kg, 1.7 mol), and palladium acetate (31.5 g, 0.14 mol) were charged, and the pressure was reduced to 40.0 kPa under stirring. After reducing the pressure, internal temperature was raised to 120° C. by steam heating. When the internal temperature reached 120° C., formylated 2,7-octadien-1-ol (8158.6 kg, 52.91 kmol) which had been charged into a 5000 L reactor separately in several times in advance, and a solution of 20% by mass tricyclohexylphosphine in xylene (63.3 kg, 37.9 kmol) were added dropwise into the system using feed pumps. The dropwise addition was carried out while the distillate and the reaction solution were analyzed by gas chromatography. After completion of the dropwise addition, crude 1,7-octadiene (5668.1 kg, yield: 90%) was obtained as a distillate. It was distilled under normal pressure, to obtain crude 1,7-octadiene (4600 kg; 95.4% in gas chromatography simple area %, 1,6-octadiene: 4.5% in gas chromatography simple area %) as a distillate at a boiling point of 117 to 118° C.

Example 5

Brominating agent=5,5-dimethyl-1,3-dibromohydantoin; in the presence of methanol Into a nitrogen-substituted 1000 mL volume flask, 1,7-octadiene (46 g) (95.4% in gas chromatography simple area %, net: 44.0 g, 0.40 mol; 1,6-octadiene: 4.5% in gas chromatography simple area %) obtained by the technique of Synthesis Example 3, and methanol (200 g) were charged. After the mixture was cooled to 10° C., 5,5-dimethyl-1,3-dibromohydantoin (11.4 g, 40.0 mmol) was added thereto at a temperature in a range of 10 to 20° C. over 3.0 hours.

After completion of the addition and stirring at a temperature in a range of 10 to 20° C. for 1.0 hour, the reaction mixture was washed with 5% by mass sodium carbonate aqueous solution (150 g). Into the reaction mixture, hexane (120 g) was added, stirred for 1.0 hour, and then left as it was, to separate an organic layer. The organic layer was washed again with 5% by mass sodium carbonate aqueous solution (150 g). The crude product was quantitatively analyzed to find out 1,7-octadiene (30.0 g) (yield: 68%, simple area ratio by gas chromatography of 1,7-octadiene to 1,6-octadiene was 0.4%) was obtained.

Synthesis Example 4

Synthesis of methyl 7-octenoate from 7-octenal

Crude 7-octenal (30.5 g) (90.0% in gas chromatography simple area %, net: 27.5 g, 0.22 mol; cis-6-octenal: 4.7% in gas chromatography simple area %, and trans-6-octenal: 4.5% in gas chromatography simple area %) was dissolved in 95% by mass acetone aqueous solution (300.0 g). After adding Jones reagent (3M chromic acid-sulfuric acid aqueous solution) (100.0 mL) and stirring at room temperature for 2 hours, isopropanol (20.0 g) was added thereto. After the precipitate was filtered off and acetone was distilled off from the filtrate, the filtrate was extracted with ethyl acetate. After the ethyl acetate layer was washed with water and saturated sodium chloride solution, the solvent was distilled off to obtain a crude product. Subsequently, this product was dissolved in methanol (300.0 g). After adding p-toluenesulfonic acid mono hydrate (3.0 g) thereto, the solution was heated at 60° C. for 2 hours. The solution was extracted with ethyl acetate, and the organic layer was washed with water and sodium carbonate aqueous solution. After that, the organic layer obtained by distilling off the solvent was distilled under a reduced pressure of 500 Pa. With this procedure, crude methyl 7-octenoate (34.3 g) (90.0% in gas chromatography simple area %, net: 30.9 g, net: 0.20 mol, yield: 91%; cis-6-octenonitrile: 4.7% in gas chromatography simple area %, and trans-6-octenonitrile: 4.5% in gas chromatography simple area %) was obtained as a distillate.

Example 6

Brominating agent=5,5-dimethylo-1,3-dibromohydantoin; in the presence of methanol Into a nitrogen-substituted 500 mL volume flask, crude methyl 7-octenoate (51.5 g) (91.0% in gas chromatography simple area %, net: 46.8 g, 0.30 mol; methyl cis-6-octenoate: 5.0% in gas chromatography simple area %, and methyl trans-6-octenoate: 3.5% in gas chromatography simple area %) obtained by the technique of Synthesis Example 4, and methanol (80.5 g) were charged. After the mixture was cooled to 0° C., 5,5-dimethyl-1,3-dibromohydantoin (10.2 g, 35.7 mmol) was added thereto at a temperature in a range of 0 to 5° C. over 6.5 hours.

After completion of the addition, the reaction mixture was washed by adding 5% by mass sodium carbonate aqueous solution (130 g). Into the reaction mixture, toluene (130 g) was added, stirred for 1.0 hour, and then left as it was, to separate an organic layer. The organic layer was washed again with 5% by mass sodium carbonate aqueous solution (130 g). The organic layer was distilled under a reduced pressure of 660 Pa to obtain high purity methyl 7-octenoate (15.3 g) (purity: 99.0%; simple area ratio by gas chromatography of methyl cis-6-octenoate to crude methyl 7-octenoate was 0.22%, and simple area ratio by gas chromatography of methyl trans-6-octenoate to crude methyl 7-octenoate was 0%) as a distillate at a boiling point of 47 to 49° C.

Comparative Example

Distillation Purification of Crude 7-octenal

Into a nitrogen-substituted 3000 mL volume of flask, crude 7-octenal (1.67 kg) (7-octenal: 93.6% in gas chromatography simple area %, net: 1.56 kg; cis-6-octenal: 1.1% in gas chromatography simple area %, and trans-6-octenal: 0.8% in gas chromatography simple area %) obtained by the technique of Synthesis Example 1 was charged. This crude 7-octenal was distilled using a distillation column packed with Heli-Pack having a height of 1 m, under a reduced pressure of 2700 Pa. However, a distillate in which content of 7-octenal was 98% or more and content of the internal olefin compound was 1 mol % or less could not be obtained. A distillate having the highest purity of 7-octenal contained 91.9 g (net: 89.4 g, yield: 5.9%; 7-octenal: 97.3% in gas chromatography simple area %, cis-6-octenal: 0.87% in gas chromatography simple area %, and trans-6-octenal: 0% in gas chromatography simple area %).

From the above, it can be shown that according to the present invention, a terminal olefin compound can be efficiently separated and purified from an internal olefin compound as an impurity by an industrially extremely advantageous technique.

It should be noted that the present application is based on JP Application No. 2009-85898 filed on 31 Mar., 2009, and the disclosure thereof has been incorporated herein in entirety by reference.

What is claimed is:
1. A method for producing a high purity terminal olefin, comprising the steps of:
(a) contacting a mixture of olefins comprising a terminal olefin and one or more internal olefins, with a brominating agent in the presence of water or an alcohol to form a reaction mixture, whereby said internal olefin(s) are converted into compounds having a higher boiling point than said terminal olefin;
and
(b) purifying said terminal olefin by distillation from said reaction mixture;
wherein said terminal olefin is represented by formula (I):

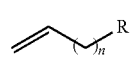

(1)

wherein n is an integer of 1 to 6, R represents —CH$_2$CH$_3$, —CH=CH$_2$, —CH$_2$CN, or —CH$_2$COR$^1$,
wherein R$^1$ is selected from the group consisting of hydrogen, alkyl having 1 to 8 carbon atoms, cycloalkyl having 3 to 8 carbon atoms, and alkoxy having 1 to 8 carbon atoms.
2. The method of claim 1, wherein said one or more internal olefins are isomers of said external olefin.

3. The method according to claim 1, wherein said terminal olefin comprises 7-octenal, and said internal olefin comprises cis- and/or trans-6-octenal.

4. The method according to claim 1, wherein said brominating agent comprises one or more compounds selected from the group consisting of N-bromoimides, dibromohydantoins, hypobromites, and alkali metal bromide/hypochlorite mixtures.

5. The method according to claim 3, wherein said brominating agent comprises one or more compounds selected from the group consisting of N-bromoimides, dibromohydantoins, hypobromites, and alkali metal bromide/hypochlorite mixtures.

6. The method according to claim 4, wherein said brominating agent comprises 5,5-dimethyl-1,3-dibromohydantoin.

7. The method according to claim 5, wherein said brominating agent comprises 5,5-dimethyl-1,3-dibromohydantoin.

* * * * *